(12) United States Patent
Ding

(10) Patent No.: US 9,675,737 B2
(45) Date of Patent: Jun. 13, 2017

(54) METHODS OF PROVIDING ANTIOXIDANTS TO A DRUG CONTAINING PRODUCT

(75) Inventor: Ni Ding, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 1023 days.

(21) Appl. No.: 12/851,420

(22) Filed: Aug. 5, 2010

(65) Prior Publication Data

US 2010/0300903 A1   Dec. 2, 2010

Related U.S. Application Data

(62) Division of application No. 11/189,216, filed on Jul. 25, 2005, now Pat. No. 7,785,647.

(51) Int. Cl.
| A01N 25/34 | (2006.01) |
|---|---|
| A61F 13/00 | (2006.01) |
| B65D 81/24 | (2006.01) |
| A61L 31/10 | (2006.01) |

(52) U.S. Cl.
CPC ......... *A61L 31/10* (2013.01); *Y10T 428/1307* (2015.01)

(58) Field of Classification Search
USPC .................................. 424/412, 422; 206/210
See application file for complete search history.

(56) References Cited

U.S. PATENT DOCUMENTS

| 3,429,717 A | 2/1969 | Cook |
|---|---|---|
| 3,993,622 A | 11/1976 | Brunetti |
| 4,401,804 A | 8/1983 | Wooten et al. |
| 5,006,281 A | 4/1991 | Rubin et al. |
| 5,288,711 A | 2/1994 | Mitchell et al. |
| 5,527,337 A | 6/1996 | Stack et al. |
| 5,539,081 A | 7/1996 | Gruber et al. |
| 5,581,387 A | 12/1996 | Cahill et al. |
| 5,618,866 A | 4/1997 | Prabhu et al. |
| 5,992,000 A | 11/1999 | Humphrey et al. |
| 6,037,022 A | 3/2000 | Adur et al. |
| 6,065,597 A | 5/2000 | Pettersson et al. |
| 6,309,383 B1 | 10/2001 | Campbell et al. |
| 6,485,950 B1 | 11/2002 | Kumar et al. |
| 6,608,187 B2 | 8/2003 | Nelson et al. |
| 6,727,300 B2 | 4/2004 | Sassi |
| 6,746,622 B2 | 6/2004 | Yang et al. |
| 6,875,400 B2 | 4/2005 | Speer |
| 6,949,254 B2 | 9/2005 | Gen |
| 7,022,258 B2 | 4/2006 | Yang et al. |
| 7,704,518 B2 | 4/2010 | Tamarkin et al. |
| 7,785,647 B2 | 8/2010 | Ding |
| 8,128,688 B2 | 3/2012 | Ding et al. |
| 8,207,240 B2 | 6/2012 | Lambert et al. |
| 8,394,446 B2 | 3/2013 | Ding |
| 2002/0015542 A1 | 2/2002 | Bradley |
| 2002/0022144 A1 | 2/2002 | Yang et al. |
| 2002/0081228 A1* | 6/2002 | Hui et al. ............... 422/3 |
| 2002/0153511 A1 | 10/2002 | Cotterman et al. |
| 2003/0083646 A1* | 5/2003 | Sirhan et al. ............. 604/891.1 |
| 2003/0144145 A1 | 7/2003 | Yang et al. |
| 2003/0189192 A1 | 10/2003 | Girelli et al. |
| 2003/0204239 A1* | 10/2003 | Carlyle et al. ............ 623/1.11 |
| 2003/0215564 A1 | 11/2003 | Heller et al. |
| 2003/0216806 A1 | 11/2003 | Togawa et al. |
| 2004/0033269 A1 | 2/2004 | Hei et al. |
| 2004/0116332 A1 | 6/2004 | Ornberg et al. |
| 2004/0220660 A1 | 11/2004 | Shanley et al. |
| 2005/0004663 A1 | 1/2005 | Llanos et al. |
| 2005/0037048 A1 | 2/2005 | Song |
| 2007/0020380 A1 | 1/2007 | Ding |
| 2007/0198080 A1 | 8/2007 | Ding et al. |
| 2009/0319031 A1 | 12/2009 | Wang et al. |
| 2010/0036047 A1 | 2/2010 | Janowicz et al. |
| 2010/0300903 A1 | 12/2010 | Ding |

FOREIGN PATENT DOCUMENTS

| JP | 2003-253031 | 9/2003 |
|---|---|---|
| WO | WO 98/41559 | 9/1998 |
| WO | WO 01/90202 | 11/2001 |
| WO | WO 03/053171 | 7/2003 |
| WO | WO 2004/050795 | 6/2004 |
| WO | WO 2005/016399 | 2/2005 |

OTHER PUBLICATIONS

International Search Report for PCT/US2006/027050, mailed Apr. 16, 2007, 9 pgs.
Ethylene oxide, Sterilization microbiology, Wikipedia, downloaded from: http://en.wikipedia.org/wiki/Sterilization_(microbiology), Apr. 24, 2012, 1 pg.
Lazada, Water Dessicant Pack (Anti-Fog), 2013, Lazada.com, www.lazada.com.my/Watershot-Desiccant-Pack-Anti-Fog-451390.html.
Mayzo "BNX® MD-1024 Antioxidant & Metal Deactivator", product data sheet, 3 pgs. (2005).
Romanova et al., "Study of antioxidant effect of apigenin, luteolin and quercetin by DNA protective method", Neoplasma 48(2) pp. 104-107 (2001).

\* cited by examiner

*Primary Examiner* — Adam C Milligan
(74) *Attorney, Agent, or Firm* — Squire Patton Boggs (US) LLP

(57) ABSTRACT

A method of providing an antioxidant to a medical device and a kit are described.

11 Claims, 2 Drawing Sheets

METHODS OF PROVIDING ANTIOXIDANTS TO A DRUG CONTAINING PRODUCT

CROSS REFERENCE

This application is a divisional application of U.S. application Ser. No. 11/189,216 filed on Jul. 25, 2005, now U.S. Pat. No. 7,785,647 the teaching of which is incorporated by reference herein in its entirety.

BACKGROUND OF THE INVENTION

Field of the Invention

This invention generally relates to a method of providing a volatile antioxidant (e.g., butylated hydroxytoluene (BHT) and/or butylated hydroxyanisole (BHA)) to a package with a medical device such as a drug-delivery stent.

Description of the Background

Drug delivery stent is becoming a common practice to treat, prevent or ameliorate a cardiovascular condition or a related medical condition. In manufacture of drug coated stent, the drug or drug-polymer formulation is first applied onto the stent as a coating. The stent then undergoes many post coating treatments, which may involve heat, moisture, pressure, sterilized gas, electron beam or radiation. After the stents are packaged, it will face shelf life challenges. For example, if a drug is oxygen sensitive, oxidation degradation may occur during these steps. One of the commonly used methods to circumvent these shortcomings is to include one or more antioxidants in the stent coating formulation. Butylated hydroxytoluene (BHT) and butylated hydroxyanisole (BHA) are commonly used antioxidant in food industry. For instance, many drugs such as limus family (e.g. everolimus, sirolimus, ABT 578, biorolimus) and paclitaxel are oxygen sensitive. To preserve the drug integrity, antioxidant was introduced into the drug coating formulation. Among them are BHT and BHA.

BHA is a volatile solid with melting temperature of 45 to 63° C. BHT can be sublimated at temperatures under its melting point (70° C.). Studies have shown that in some stent coating processes, up to 40% BHT may be lost during standard ethylene oxide (ETO) sterilization process, which involves heat and moisture.

Therefore, there is a need for the preservation of BHT and/or BHA in a stent manufacturing process. There is another need for the incorporation of BHT and/or BHA into the drug product.

The embodiments described below address the above described problems and needs.

SUMMARY OF THE INVENTION

Provided herein is a method for providing a volatile antioxidant (e.g., BHT and/or BHA) to a medical device (e.g., drug delivery stent) during and/or after the manufacturing process of the device. The method includes adding an antioxidant (e.g., BHT and/or BHA) to a medical device or a coating for the device, causing the antioxidant to permeate into a medical device or a coating for the device, or otherwise providing an antioxidant in the proximity or surrounding of a medical device (e.g., a stent). In some embodiments, the antioxidant permeates into a medical device or a coating of the medical device so as to provide the antioxidant in the device and/or coating or to enhance the content of the antioxidant in the device and/or coating. The antioxidant can be the same or different from the antioxidant in the device or coating should the device or coating already include one.

The medical device can be a stent that can be a metallic or polymeric stent which is biodegradable or nondegradable. The stent itself or a coating on the stent may include a bioactive agent such as paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), pimecrolimus, 40-O-(3-hydroxy) propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, bioactive RGD, CD-34 antibody, abciximab (REOPRO), progenitor cell capturing antibody, prohealing drugs, prodrugs thereof, co-drugs thereof, or a combination thereof.

DETAILED DESCRIPTION

Provided herein is a method for providing an antioxidant (e.g., a volatile antioxidant), in some embodiments, butylated hydroxytoluene (BHT) and/or butylated hydroxyanisole (BHA), to a medical device such as a drug delivery stent or to a coating on the device during the manufacturing process or storage of the device. In some embodiments, the method includes causing an antioxidant (e.g., BHT and/or BHA) to permeate into a medical device or a coating on the device or otherwise providing an antioxidant in the proximity of a medical device (e.g., a stent) to allow the antioxidant to permeate into the medical device or the coating of the medical device so as to provide the antioxidant to the device or the coating or to enhance the content of the antioxidant in the device or the coating. The device or coating can include a drug. The antioxidant can be the same or different from the antioxidant in the device or coating should the device or the coating already include one. In some embodiments, the device or coating does not include an antioxidant such that the method provides for one to be added in the device or coating. In some other embodiments, the antioxidant added to a medical device or coating by the method described herein may compensate the whole or part of the loss of the antioxidant in the medical device (e.g., stent) or coating during the manufacture or storage of the medical device. In one embodiment, the antioxidant is added to the device or coating in an amount more than the loss of the antioxidant in the medical device or coating from the manufacturing process or during storage.

Figure 1:
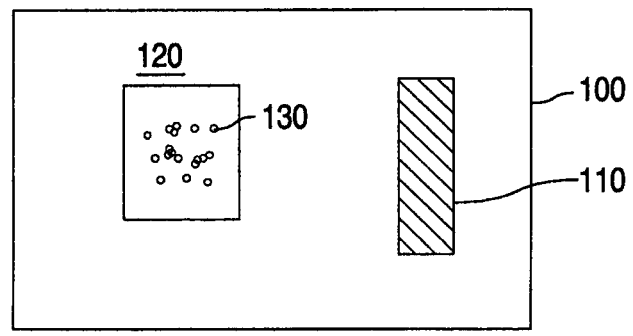
FIG. 1 shows one embodiment of the present invention where an antioxidant is placed in a porous or permeable container in a product package containing a medical device.

The medical device can be a stent that can be a metallic or polymer stent. The stent can be a biodegradable stent or a nondegradable stent. The stent may have a polymeric coating that may include a bioactive agent such as everolimus. The coating can be biodegradable or nondegradable. In some embodiments, the stent, itself, can be a polymeric biodegradable, bioerodable or bioabsorbable stent, terms which are used interchangeably unless specifically indicated, which can include the bioactive agent embedded in the body of the stent or coating in the stent. The stent can be intended for neurovasculature, carotid, coronary, pulmonary, aorta, renal, biliary, iliac, femoral, popliteal, or other peripheral vasculature. The stent can be used to treat, prevent, or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof Permeation of a Volatile Antioxidant into a Coating In one embodiment, an amount (e.g., ranging from about 1 mg to about 10 g) of a volatile antioxidant can be placed in a porous or permeable container and then place the container inside a product package such as a Tyvek pouch within which a medical device (e.g., stent) is packaged. This embodiment is shown in FIG. 1, where the Tyvek package 100 contains a stent 110 and a porous or permeable container 120, which contains antioxidant 130. Thus, in one commercial embodiment, a kit is provided having a sterile device, such as a drug delivery stent, and an antioxidant included in the kit packaging. The stent can be packaged alone or may be pre-crimped on a delivery catheter or a balloon catheter, ready for use by a health care provider. The figures do not illustrate a catheter assembly for delivery of the stent but such devices are well known to one having ordinary skill in the art. For example, permeation of BHT into a polymeric coating can be achieved by placing a certain amount (e.g., 500 mg) of BHT in a porous or permeable container and placing the container inside a Tyvek pouch within which a medical device such as a stent is packaged prior to ethylene oxide (ETO) sterilization. During the ETO process (typically at 55° C.), BHT sublimates to form a BHT gas. The BHT gas then fills in the Tyvek pouch. The permeation rate of molecules through a Tyvek pouch is size sensitive. Larger molecules have a smaller permeation rate while smaller molecules have a larger permeation rate. Permeation rate of ETO, cresol and toluene on one kind of Tyvek material are listed below as examples of molecular size dependence on the permeation rate (Table 1).

TABLE 1

| Material | Time to reach permeation rate of 1 µg/cm²/min |
|---|---|
| ETO | 120 |
| Cresol | 206 |
| Toluene | >480 |

Since BHT is much more bulky than ethylene oxide, it is expected that the permeation rate for BHT is significantly lower than ethylene oxide gas. Depending on the type of Tyvek pouch, the permeation rate for ETO gas and moisture could be significantly different from the bulky BHT molecule. Accordingly, over time, the Tyvek pouch can be over-saturated with BHT, which could reduce the escape of BHT from coated stents and even may lead to reverse diffusion of BHT into a coating such as the coating of a drug-delivery stent, increasing BHT content in the coating of the stent. Should the coating not include an antioxidant, such process may lead to the incorporation of the antioxidant into the coating. In some embodiments, prior to the use of the device, the level of antioxidant can be lower than the initial level of the antioxidant. In some embodiments, as mentioned previously, the level is higher. It is also possible that the level of antioxidant is preserved, e.g., about ±5%, about ±10%, about ±15%, about ±20%, or about ±30%.

Figure 2:
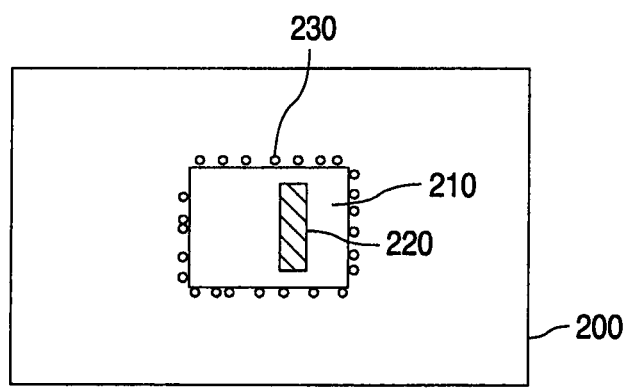
FIG. 2 shows another embodiment of the present invention where an antioxidant is present between the product packaging that includes a medical device and a secondary packaging in that the antioxidant is placed in the outer layer of the product packaging.

In another embodiment, an amount (e.g., an amount from about 1 mg to about 20 g) of an antioxidant or a volatile antioxidant (e.g., BHT and/or BHA) can be placed intimately close to a medical device, such as bioerodable polymeric stent or polymeric coated metallic stent, which is packaged within a package (e.g., Tyvek package), in a gas impermeable secondary package after sterilization. In some embodiments, it can be before sterilization. As shown in FIG. 2, the secondary packaging 200 encloses a Tyvek packaging 210, which includes a stent 220. The kit can include the stent 220 by itself or pre-crimped on a delivery catheter or balloon catheter. On the outer layer of the Tyvek packaging 210, an antioxidant 230 is placed. The gas impermeable secondary package can be made of any plastic or non-plastic material. In this embodiment, the volatile antioxidant (e.g., BHT and/or BHA) evaporates over time, fills the space and prevents the infiltrated oxygen from damaging the product. To speed up the sublimation, one may optionally heat the entire finished package to a temperature e.g., e.g., between 20° C. and, 70° C. (e.g., about 30° C., about 40° C., about 50° C., or about 60° C.) for a short period of time (e.g., about 10 seconds, about 20 seconds, about 30 seconds, about 40 seconds, about 50 seconds, about 60 seconds, about 90 seconds, or about 120 seconds) to allow enough antioxidant gas (e.g., BHT gas) to fill the space of the secondary package. The heating can be achieved by any heating means known in the art. It is noteworthy that, in this embodiment, the volatile antioxidant (e.g., BHT) is not added directly to the polymer and/or drug formulation.

Figure 3:
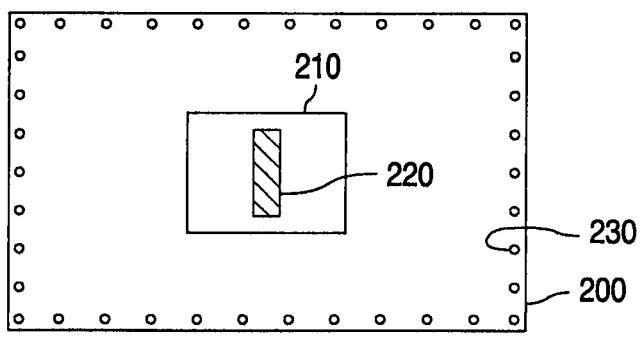
FIG. 3 shows another embodiment of the present invention where an antioxidant is present between the product packaging that includes a medical device and a secondary packaging in that the antioxidant is placed in the inner layer of the secondary packaging.

In another embodiment, the shelf life of a medical device (e.g., stent) can be improved by providing a gas impermeable secondary package, placing (e.g., by coating) an amount (e.g., about 1 mg to about 20 g) of an antioxidant (e.g., BHT particles or BHT film) in the inner-layer or inside of the secondary package, and placing a sterilized product package (e.g., Tyvek package) containing a drug-delivery stent that can include a antioxidant (e.g., BHA and/or BHT) into the secondary package. The sterilization can be by commonly known techniques including ETO. In some embodiments, sterilization can be subsequent to placement in the secondary package. As shown in FIG. 3, the secondary packaging 200 encloses a Tyvek packaging 210, which includes a stent 220. On the inner layer or inside of of the secondary packaging 200, an antioxidant 230 is placed. The antioxidant will then evaporate to form a vapor which protects the enclosed product. The antioxidant can be the same or different from the antioxidant in the medical device. As with any other embodiments of the invention, such embodiment can be in the form of a labeled medical kit with a stent or the stent premounted on a delivery or balloon catheter.

In a further embodiment, the product shelf life can be prolonged by placing (e.g., by coating) an amount (e.g., about 1 mg to about 20 g) of a volatile antioxidant (e.g., BHT particles or BHT film) on the outer layer of a product package (e.g., Tyvek package) containing a medical device (e.g., stent) that can include a antioxidant and placing the product package inside a gas impermeable secondary package. The medical device can be sterilized prior to placement in the secondary package or alternatively after its placement. The antioxidant then evaporates over the time to protect the drug from oxidation. It should be noted that the antioxidant can be added between the two packaging in solid, fluid or gas form and is not limited to a coating form. The antioxidant can be the same or different from the antioxidant in the medical device should the device already include one. Unless otherwise specifically indicated, the term "gas impermeable" means impermeable to an antioxidant gas, preferably to BHT or BHA (conversely, the term "permeable" means permeable to an antioxidant gas). Again, such an assembly can be in the form of a medical kit with a stent or the stent premounted on a catheter.

In a further embodiment, an antioxidant can be added to the formulation from which the device is made or from which the device is coated. For example, the antioxidant can be added to the polymer/solvent coating formulation with or without a drug. The formulation could be used to form the reservoir layer or a topcoat layer on top of the reservoir layer. The topcoat layer can be free of drug although in certain circumstances some drug migration might occur.

The method described herein is applicable to any medical device coated with one or more drugs or bioactive agents with or without a polymeric material and optionally with one or more biobeneficial materials. The drug can be blended, conjugated, bonded or combined with a polymer. The method described herein is also applicable to any biodurable or bioabsorable (which can include bioerodable or biodegradable) device formed of a polymeric material optionally with one or more bioactive agents. The drugs or agents can be compounded in the body of the device or coated on the device. The biocompatible polymer useful for forming a coating composition can be any biocompatible polymer known in the art, which can be biodegradable or nondegradable. Biodegradable is intended to include bioabsorbable or bioerodable, unless otherwise specifically stated. Representative examples of polymers that can be used to coat a medical device in accordance with the present invention include, but are not limited to, poly(ester amide), ethylene vinyl alcohol copolymer (commonly known by the generic name EVOH or by the trade name EVAL), poly(L-lactide), poly(D-lactide), poly(D,L-lactide), poly(D,L-lactide-co-L-lactide), poly(L-lactide-co-glycolide), poly(D,L-lactide-co-glycolide) (PDLLAGA), poly(L-lactide-co-caprolactone), poly(D,L-lactide-co-caprolactone), poly(hydroxyvalerate), polycaprolactone, poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, fluoro polymers or copolymers under the trade name Solef™ or Kynar™ such as polyvinylidene fluoride (PVDF) and poly (vinylidene fluoride-co-hexafluoropropylene), polyvinylidene chloride, poly(butyl methacrylate), polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, isobutylene-styrene copolymers, methacrylate-styrene copolymer, ABS resins, and ethylene-vinyl acetate copolymers, polyamides, such as Nylon 66 and polycaprolactam, alkyd resins, polycarbonates, polyoxymethylenes, polyimides, polyethers, polyvinylpyrrolidone (PVP), poly(vinyl alcohol) (PVA), polyacrylamide (PAAm), poly(glyceryl sebacate), polypropylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

The biocompatible polymer can provide a controlled release of a bioactive agent, if included in the coating and/or binding the bioactive agent to a substrate, which can be the surface of a medical device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,581,387 to Labrie, et al.). The release rate of the bioactive agent can be controlled by, for example, by selection of a particular type of biocompatible polymer which can provide a desired release profile of the bioactive agent. The release profile of the bioactive agent can be further controlled by the molecular weight of the biocompatible polymer and/or the ratio of the biocompatible polymer over the bioactive agent. In the case of a biodegradable polymer, the release profile can also be controlled by the degradation rate of the biodegradable polymer. One of ordinary skill in the art can readily select a carrier system using a biocompatible polymer to provide a controlled release of the bioactive agent.

A preferred biocompatible polymer is a polyester, such as one of poly(ester amide), poly(D,L-lactide) (PDLLA), poly (D,L-lactic acid-co-glycolic acid) (PDLLGA), polyglycolic acid (PGA), polyhydroxyalkanoate (PHA), poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), poly(D,L-lactide), poly(L-lactide), polycaprolactone (PCL) and a combination thereof.

The biobeneficial material can be a polymeric material or non-polymeric material. The biobeneficial material is preferably flexible when present as a discrete layer, or confers elastic properties in a blend or copolymer, and is biocompatible and/or biodegradable, more preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent. As used herein, the term non-fouling is defined as preventing, delaying or reducing the amount of formation of protein build-up caused by the body's reaction to foreign material and can be used interchangeably with the term "anti-fouling."

Representative biobeneficial materials include, but are not limited to, polyethers such as poly(ethylene glycol), copoly (ether-esters) (e.g. PEO/PLA); polyalkylene oxides such as poly(ethylene oxide), polypropylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropyl methacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), polystyrene-polyisoprene-polystyrene-co-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof. In some embodiments, the biobeneficial material can exclude any one of the aforementioned materials.

In a preferred embodiment, the biobeneficial material is a block copolymer comprising flexible poly(ethylene glycol terephthalate)/poly(butylenes terephthalate) (PEGT/PBT) segments (PolyActive™). These segments are biocompatible, non-toxic, non-antigenic and non-immunogenic. Previous studies have shown that the PolyActive™ top coat decreases the thrombosis and embolism formation on stents. PolyActive™ is generally expressed in the form of xPEG-TyPBTz, in which x is the molecular weight of PEG, y is percentage of PEGT, and z is the percentage of PBT. A specific PolyActive™ polymer can have various ratios of the PEG, ranging from about 1% to about 99%, e.g., about 10% to about 90%, about 20% to about 80%, about 30% to about 70%, about 40% to about 60% PEG. The PEG for forming PolyActive™ can have a molecular weight ranging from about 300 Daltons to about 100,000 Daltons, e.g., about 300 Daltons, about 500 Daltons, about 1,000 Daltons, about 5,000 Daltons, about 10,000 Daltons, about 20,000 Daltons, or about 50,000 Daltons.

In another preferred embodiment, the biobeneficial material can be a polyether such as polyethhylene glycol (PEG) or polyalkylene oxide.

The bioactive agents can be any diagnostic, preventive and therapeutic agents. Examples of such agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of drugs include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Such agents can also include a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. Such agents can also fall under the genus of antineoplastic, cytostatic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include heparinoids, hirudin, recombinant hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, and thrombin inhibitors such as Angiomax ä (Biogen, Inc., Cambridge, Mass.). Examples of cytostatic agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other drugs include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, bioactive RGD, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, antivirals, anticancer drugs, anticoagulant agents, free radical scavengers, steroidal anti-inflammatory agents, nonsteroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), dexamethasone, clobetasol, aspirin, estradiol, tacrolimus, rapamycin, rapamycin derivatives, 40-O-(2-hydroxy)ethyl-rapamycin (everolimus), pimecrolimus, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), pimecrolimus, imatinib mesylate, midostaurin, progenitor cell capturing antibody, pro-drugs thereof, co-drugs thereof, and a combination thereof. The foregoing substances are listed by way of example and are not meant to be limiting. Other active agents which are currently available or that may be developed in the future are equally applicable.

Examples of Medical Device

As used herein, a medical device may be any suitable medical substrate that can be implanted in a human or veterinary patient. Examples of such medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structures can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. For example, the device can be a bioabsorbable stent, made from a polymeric material (and optionally erodable metal). The bioabsorbable stent can include a drug coating, for example with a polymer film layer or the drug can be compounded or embedded in the body of the stent.

Method of Use

A medical device (e.g., stent) having any of the above-described features is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, restenosis, and vulnerable plaque. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having with or without a drug delivery coating may then be expanded at the desired area of treatment. A post-insertion angiogram may also be utilized to confirm appropriate positioning.

EXAMPLE

Study of BHT Loss in the Stent Manufacture Process

Experiment Results and Discussion
Table 2 listed sampling schemes for the tested sample stents.

TABLE 2

Sampling scheme

| Stent Label | Sampling steps | # of stent for BHT test | # of stent for drug content |
|---|---|---|---|
| 1 | After stent secured on the balloon and packaged in Tyvek pouch | 5 | 4 |
| 2 | After ETO sterilization | 5 | 4 |

Besides the sampling scheme for stents, BHT amount in the drug substance and in the coating solution was also assayed. The stents were manufactured by following standard Guidant procedures, which included drug coat solution mixing, spray coating, drying, stent retention on the balloon catheters, and packaging of coated stent device in Tvyek pouch.

Table 3 is a summary of BHT and total content of the drug (TC) test results at the various stages of stent manufacture process.

TABLE 3

Summary of BHT and TC test results

| Groups | Conditions | TC, % | BHT found, ng/ug drug | % BHT retained | % BHT loss |
|---|---|---|---|---|---|
|  | Raw drug |  | 1.78 | 100 | 0 |
|  | Drug coat solution |  | 1.80 | 101.1 | 0 |
| 1 | before ETO | 98.5 | 0.97 | 54.6 | 45.4 |
| 2 | Post ETO | 94.8 | 0.11 | 5.9 | 94.1 |

The percent BHT was normalized based on BHT in raw drug substance. The results showed that the drug mixing process did not change BHT content. About 45% BHT was lost during stent spray coating, drying and stent retention process. With conventional ETO process, BHT dropped from ~50% to ~5% before and after ETO. Total content recovery was correlated with BHT level. The higher the BHT amount in the stents, the higher the total content recovery of the drug, indicating missing total content of the drug might be related to oxidation of the drug.

Figure 4:
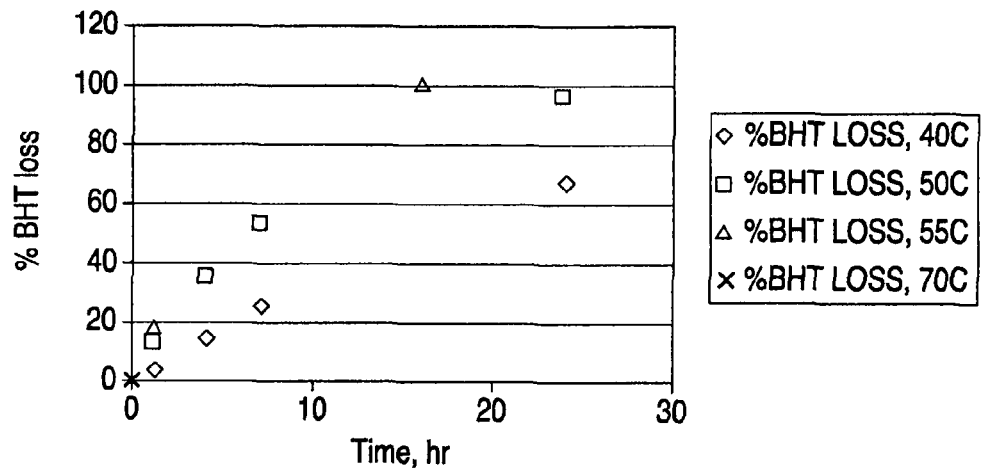
FIG. 4 shows butylated hydroxytoluene (BHT) powder sublimation at different temperature.
Figure 5:
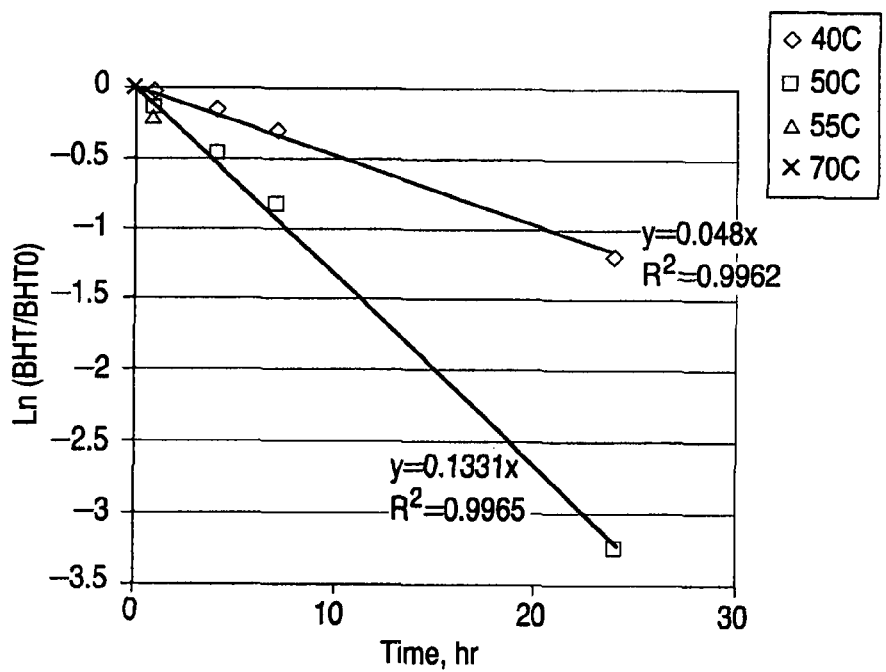
FIG. 5 shows BHT retained in a coating at different temperatures.

Since BHT loss in ETO process was severe, a study was designed to determine the cause. 100 mg of BHT was weighed in an aluminum pan and baked in a convectional oven at 55° C. and checked at 1 hr and 16 hr. The pan was weighed after each time point. After overnight baking, all the BHT powder was gone. The experiment was repeated at 70° C. for 30 minutes and 1 hr. Since 70° C. is the melting temperature for BHT, the results represented the worst case. The experiment was redone at 40° C. and 50° C. for 1 hr, 4 h, 7 h and 24 h. FIG. 4 is the plot of BHT weight loss vs. time at various temperatures. As shown in FIG. 4, it is clear that BHT sublimation occurred at temperatures under 70° C. FIG. 5 is a plot of Ln (BHT/BHT$_0$) vs. time. Linearity was seen at 40° C. and 50° C. baking, indicating first order sublimation kinetics. No curve fitting was performed on 55° C. and 70° C. experiment conditions, due to not enough data points. Equation 1 represents $1^{st}$ order kinetics, $$\text{Ln} \frac{BHT}{BHT_0} = -kt \qquad (1)$$

where $BHT/BHT_0$ is the ratio of BHT remained in the pan at time t and k is the sublimation rate constant at the experiment temperature. Using equation 1, the half-lives for BHT sublimation are ~13 hr at 40° C. and ~5 hr at 50° C.

Based on the curve fitting in FIG. 5, $k_{40C}$=0.048 and $k_{50C}$=0.1331. Using Arrhenius equation (Equation 2), $$\text{Ln}\frac{k_2}{k_1} = \frac{E_a}{R}\left[\frac{T_2 - T_1}{T_1 T_2}\right] \quad (2)$$

where R is the gas constant (1.987) and $E_\alpha$ is the sublimation activation energy, the activation energy for BHT sublimation is 20.5 kcal/mol. The rate constant at other temperatures can be readily calculated with equations 1 and 2.

The sublimation energy for BHT is about 2 times of water's heat of vaporization, which is not very high. The experiment explained why BHT got lost during ETO process. Long time exposure of stents at 55° C. during ETO process can cause sublimation of BHT. With polymer protection, the sublimation rate was largely reduced.

The study showed that ETO process contributed heavily on BHT loss. It also demonstrated the relationship between total content recovery and BHT levels on the stent. The study also demonstrated that one could take advantage of the volatile nature of BHT and BHA to enhance the product performance by placing or coating BHT/BHA in the secondary package. Other benefits include increase in storage life of the product.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A kit, comprising:
   a pouch;
   a medical device with a drug in the pouch;
   a porous or permeable container in the pouch; and
   an antioxidant in the porous or permeable container such that the medical device with the drug is placed outside of the porous or permeable container;
   wherein the antioxidant is a volatile antioxidant and evaporates and fills the space of the pouch.

2. The kit according to claim 1, wherein the antioxidant comprises butylated hydroxytoluene (BHT), butylated hydroxyanisole (BHA) or a combination thereof.

3. The kit according to claim 1, wherein the antioxidant is of a type to sublime to form a gas that permeates out from the container.

4. The kit according to claim 1,
   wherein the antioxidant of claim 1 is a first antioxidant; and
   wherein the medical device or the drug comprises a second antioxidant, the second antioxidant being the same as or different than the first antioxidant, such that the first antioxidant is adapted to be added to the medical device or the drug subsequent to a loss of the second antioxidant from the medical device or the drug during the life of the medical device or the drug in the pouch.

5. The kit according to claim 1, wherein the medical device comprises a stent.

6. The kit according to claim 1, wherein the medical device comprises a coated stent.

7. The kit according to claim 1, wherein the coating comprises the drug.

8. The kit according to claim 7, wherein the drug is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), pimecrolimus, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), imatinib mesylate, midostaurin, clobetasol, bioactive RGD, CD-34 antibody, abciximab (REOPRO), progenitor cell capturing antibody, and prodrugs and combinations thereof.

9. The kit of claim 6, wherein the coated stent is crimped on a delivery catheter or a balloon catheter.

10. The kit according to claim 1, wherein the medical device comprises a coating which comprises a biocompatible polymer.

11. The kit according to claim 10, wherein the biocompatible polymer is selected from the group consisting of poly(ester amide), ethylene vinyl alcohol copolymer, poly (D,L-lactide) (PDLLA), poly(D,L-lactic acid-co-glycolic acid) (PDLLGA), polyglycolic acid (PGA), polyhydroxyalkanoate (PHA), poly(3-hydroxybutyrate) (PHB), poly(3-hydroxybutyrate-co-3-hydroxyvalerate), poly(3-hydroxyvalerate), poly(3-hydroxyhexanoate), poly(4-hydroxybutyrate), poly(4-hydroxyvalerate), poly(4-hydroxyhexanoate), poly(D,L-lactide), poly(L-lactide), polycaprolactone (PCL), polydioxanone, polyorthoester, polyanhydride, poly(glycolic acid-co-trimethylene carbonate), and a combination thereof.

* * * * *